United States Patent [19]

Law et al.

[11] Patent Number: 4,897,209

[45] Date of Patent: Jan. 30, 1990

[54] LUBRICANT COMPOSITIONS CONTAINING ARYLSULFONIC ACIDS, AND ORGANO PHOSPHITES AND REACTION PRODUCTS THEREOF

[75] Inventors: Derek A. Law, Yardley; Shi-Ming Wu, Newtown, both of Pa.

[73] Assignee: Mobil Oil Corp., New York, N.Y.

[21] Appl. No.: 292,800

[22] Filed: Jan. 3, 1989

[51] Int. Cl.[4] .................. C01M 135/10; C01M 137/04
[52] U.S. Cl. ................. 252/32.7 E; 252/32.5; 252/46.6; 558/86; 558/218
[58] Field of Search ............ 252/46.6, 32.7 E, 32.7 R, 252/32.5, 33.3; 558/218

[56] References Cited

U.S. PATENT DOCUMENTS

| | | | |
|---|---|---|---|
| 3,082,187 | 3/1963 | Fuchsman et al. | 558/218 |
| 3,459,662 | 8/1969 | Shih-En Hu | 252/46.6 |
| 3,627,681 | 12/1971 | Chandler | 252/32.7 E |
| 4,328,111 | 5/1982 | Watson et al. | 252/32.5 |
| 4,349,445 | 9/1982 | Rosenberger | 558/86 |
| 4,814,097 | 3/1989 | Cardis | 252/46.6 |

*Primary Examiner*—William R. Dixon, Jr.
*Assistant Examiner*—Maria Reardon Nguyen
*Attorney, Agent, or Firm*—Alexander J. McKillop; Charles J. Speciale; Robert B. Furr, Jr.

[57] ABSTRACT

Disclosed are lubricant compositions containing a lubricant and:

(a) the reaction product of a metal dihydrocarbylaromatic sulfonate and a dialkyl or trialkyl phosphite; or (b) the reaction product of a metal dialkylnaphthalene sulfonate and a dialkyl or trialkyl phosphite and further containing an acid or acid supplying component; or (c) an unreacted mixture of dialkylnaphthalene sulfonic acid and a dialkyl or trialkyl phosphite.

50 Claims, No Drawings

LUBRICANT COMPOSITIONS CONTAINING ARYLSULFONIC ACIDS, AND ORGANO PHOSPHITES AND REACTION PRODUCTS THEREOF

NATURE OF THE INVENTION

This invention relates to lubricants and particularly to lubricants containing or generating arylsulfonic acids, organo phosphites and the reaction products of aryl sulfonic acids and organophosphites.

PRIOR ART

Calcium sulfonate is a known rust inhibitor and demulsifier additive for lubricating oils and greases. U.S. Pat. Nos. 4,419,251 and 4,419,252 disclose calcium dinonyl naphthalene sulfonate as a component for a lubricant concentrate for forming oil-in-water emulsions upon dilution with water. Organophosphites have been used for their extreme pressure and antiwear properties in lubricant formulations. U.S. Pat. Nos. 4,717,491 and 4,626,368 discloses the use of reaction products of dialkyl and trialkyl phosphites in lubricant compositions.

SUMMARY OF THE INVENTION

This invention comprises in one aspect a lubricant composition containing (a) the reaction product of a metal dihydrocarbylaromatic sulfonate such as a metal dialkylnaphthalene sulfonate and a dihydrocarbyl or trihydrocarbyl phosphite, such as dialkyl or trialkyl phosphite, or (b) the reaction product of a metal dihydrocarbylsulfonic acid, such as a metal dialkylnaphthalene sulfonate and a dihydrocarbyl or trihydrocarbyl phosphite, such as dialkyl or trialkyl phosphite and further containing an acid or acid supplying component, or (c) a dihydrocarbyl aromatic sulfonic acid, such as dialkylnaphthalene sulfonic acid and a dihydrocarbyl or trihydrocarbyl phosphite. Another aspect of this invention comprises the method of making the lubricant composition by incorporating any of the above described groups into a lubricant. Still another aspect of this invention comprises the reaction product of a metal dialkylnaphthalene sulfonate or dialkylnaphthalene sulfonic acid and a dialkyl or trialkyl phosphite.

DETAILED DESCRIPTION OF THE INVENTION (a) Reaction Product of Metal Dihydrocarbylaromatic Sulfonates Such As Metal Dialkylnaphthalene Sulfonate and Dihydrocarbyl or Trihydrocarbyl Phosphite The metal dialkylnaphthalene sulfonate has a sulfonate group attached to one ring of the naphthalene nucleus and an alkyl group attached to each ring. Each alkyl group can independently contain from about six to about twenty carbon atoms, but it is preferred that they contain from about eight to twelve carbon atoms. The dialkylnaphthalene sulfonate group is attached to the metal through the sulfonate group. In the case of monovalent metals, one dialkylnaphthalene sulfonate group is attached to each metal atom while there are two groups attached to each atom of a divalent metal. Calcium, barium, sodium, magnesium and lithium can be used as the metal, but calcium is often preferred as the metal in the sulfonate.

The dihydrocarbyl or trihydrocarbyl phosphite has the general formula:

$$(R_1O)_2POR_2$$

where $R_1$ is a hydrocarbon radical of 2 to 18 carbon atoms, preferably 4 to 18 carbon atoms, and $R_2$ is hydrogen or a hydrocarbon radical of 2 to 18 carbon atoms preferably 4 to 18 carbon atoms. Useful hydrocarbyl phosphites include oleyl, phenyl, nonyl phenyl, octylphenyl, 1-ethyl hexyl, 1,3-dimethylbutyl, tridecyl, isodecyl, octyl and butyl, and mixed phosphites of the above radicals. Trihydrocarbyl phosphites are often preferred over dihydrocarbyl phosphites. If desirable, an unreactive organic solvent can be utilized. Preferably the organic solvent is selected from benzene, toluene, xylene, and mixed alkyl and aromatic petroleum distillates.

In preparing the reaction product of the metal dialkylnaphthalene sulfonate and hydrocarbyl phosphite the two materials preferably are reacted at a temperature between 30° C. and 250° C., more preferably from 60° C. to 160° C. in a molar ratio of from 10:1 to 1:10 moles of sulfonate per mole of phosphite.

The reaction product thus obtained is added to the base lubricating oil stock in a concentration of between 0.01% and 10%.

(b) Reaction Product of Metal Dihydrocarbylaromatic Sulfonates, Such As Dialkylnaphthalene Sulfonate and Di-Or Trihydrocarbyl Phosphite, Such As Di or Trialkyl Phosphite And An Acid or-Acid Supplying Component The reaction product is prepared as described in (a) above and is added to the base lubricating oil along with an acid or acid source. The usable acids or acid sources include dilute sulfuric acid, as well as any other source of inorganic or organic acids such as fatty acids capable of generating proton-derived acidity. The reaction product and acid source are each added to the lube oil base stock in concentrations of 0.01% to 10% and 0.001% to 1% respectively.

(c) Unreacted Dialkylnaphthalene Sulfonic acid and Di- or Trihydrocarbyl Phosphite Added To Base Oil In this modification of the invention the dihydrocarbylaromatic sulfonic acid, such as dialkylnaphthalene sulfonic acid, and the di- or trialkyl phosphite components are not reacted but are combined directly into the lubricating oil composition and make use of acids generated during oil degradation in service. The concentration of each in the lube oil compositions is between 0.01% and 5% and between 0.01% to 5% respectively.

An important feature of the invention is the ability of the additive to improve the antiwear properties and the resistance to oxidation of a lubricating oil such as mineral oil, synthetic oils, mixtures of these, or a grease in which any of the aforementioned oils are employed as a vehicle. In general, the mineral oils, both paraffinic, naphthenic and mixtures thereof, employed as a lubricating oil or as the grease vehicle, can be of any suitable lubricating viscosity range, as for example, from about 45 SSU at 100° F. to about 6000 SSU at 100° F., and preferably from about 50 to about 250 SSU at 210° F. These oils may have viscosity indexes ranging to 100 or higher. Viscosity indexes from about 70 to about 95 are preferred. The average molecular weights of these oils can range from about 250 to about 800.

Where the lubricant is employed as a grease, the lubricating oil is generally used in an amount sufficient to balance the total grease composition, after accounting for the desired quantity of the thickening agent, and other additive components included in the grease formulation. A wide variety of materials can be employed as thickening or gelling agents. These can include any of the conventional metal salts or soaps, such as calcium, or lithium stearates or hydroxystearates, which are dispersed in the lubricating vehicle in grease-forming quantities in an amount to impart to the resulting grease composition the desired consistency. Other thickening agents that can be employed in the grease formulation comprise the non-soap thickeners, such as surface-modified clays and silicas, aryl ureas, calcium complexes and similar materials. In general, grease thickeners can be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in preference to mixtures of mineral and synthetic oils, various synthetic oils may be utilized successfully. Typical synthetic oil vehicles include polyisobutylenes, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes) and alkyl-substituted diphenyl ethers typified by a butyl-substituted bis(p-phenoxy phenyl) ether, and phenoxy phenylethers.

It is to be understood that the compositions contemplated herein can also contain other materials. For example, other corrosion inhibitors, extreme pressure agents, viscosity index improvers, coantioxidants, antiwear agents and the like can be used. These include, but are not limited to, phenates, sulfonates, succinimides, zinc dialkyl or diaryl dithiophosphates, and the like. These materials do not detract from the value of the compositions of this invention.

EXAMPLE 1

This example illustrates the preparation of the reaction product described in (a) above. Approximately 92.3 grams of commercially obtained calcium dinonylnaphthalene sulfonate commercially obtained from King Industries, Inc. as Na-sul 729) was charged to a flask equipped with thermometer, nitrogen gas sparger, condenser, and agitator and diluted with 100 ml of toluene. Tributyl phosphite (12.5 grams, 0.05 mol) was then added at room temperature, and the reaction mixture was heated and refluxed for 4 hours. The resulting product was evaporated under a reduced pressure at 110° C. resulting in a yield of 96.5 grams of viscous dark brown fluid.

EXAMPLE 2

This example illustrates preparation of the additive according to (b). Approximately 112 grams of the dinonylnaphthalene sulfonate described in Example 1 was mixed in 50 ml of toluene and acidified with 4.9 ml of 30% sulfuric acid under a nitrogen atmosphere. The mixture was heated to 60° C. for two hours and then cooled to room temperature. Tributyl phosphite (15.3 grams, 0.06 mole) was added dropwise; the reaction was slightly exothermic (from 25° C. to 31° C.), and at the end of addition, the mixture was heated and refluxed for 3 hours. The resulting mixture was diluted with 250 ml of toluene and washed with water, dried, and evaporated under a reduced pressure at 110° C. to yield 133 grams of a viscous grey-brown fluid.

EXAMPLE 3

This example also illustrates the preparation of the additive according to (b). Approximately 112 grams of the previously described sulfonate mixed in 50 ml of toluene was acidified with 4.9 ml of 30% sulfuric acid. After one hour reaction time at 60° C. dibutyl phosphite (11.9 grams, 0.6 mole) was added dropwise, and the reaction mixtures was then heated and refluxed for 3 hours. The resulting mixture was filtered, washed with toluene, and the combined filtrate and washings evaporated under a reduced pressure at 110° C. to yield 123 grams of viscous brown fluid.

EVALUATION OF PRODUCTS

The products of the examples were blended into solvent paraffinic neutral mineral oil and evaluated using proprietary methods for testing oxidative stability. Results are reported in Tables 1 & 2. The EP/antiwear properties are shown in Tables 3 and 4. Tables 1 and 2 illustrate the antioxidant characteristics of the Examples.

TABLE 1

| Item | Catalytic Oxidation Test 325° F., 40 hours | |
|---|---|---|
| | Increase in Acidity Change in Acid Number TAN* | Viscosity Increase Percent Change in Kinematic Viscosity % |
| Base oil (100% solvent paraffinic neutral mineral oil) | 6.63 | 66.3 |
| 1% of example 1 | 0.50 | 6.2 |
| 1% of example 2 | 0.34 | 6.1 |
| 1% of example 3 | −0.15 | 4.1 |

TAN = Total Acid Number

TABLE 2

| Item | Catalytic Oxidation Test 325° F., 72 hours | |
|---|---|---|
| | Increase in Acidity Change in Acid Number TAN | Viscosity Increase Percent Change in Kinematic Viscosity % |
| Base oil (100% solvent paraffinic neutral mineral oil) | 8.16 | 110.0 |
| 1% of example 1 | 1.49 | 10.4 |
| 1% of example 2 | 0.73 | 17.9 |
| 1% of example 3 | 0.09 | 14.2 |

TABLE 3

| Four - Ball Wear Test | |
|---|---|
| Item | Wear Scar Diameter in mm, 30 Minute Test, 60 kg Load, 2000 RPM, 200 F. |
| 1. 1% Calcium dinonylnaphthalene sulfonate + 1% (BuO)₃P in base oil | 2.00 |

TABLE 3-continued

Four - Ball Wear Test

| Item | Wear Scar Diameter in mm, 30 Minute Test, 60 kg Load, 2000 RPM, 200 F. |
|---|---|
| 2. 1% Calcium dinonylnaphthalene sulfonate + 1% (BuO)₃P + 0.2% H₂SO₄ in base oil | 0.57 |
| 3. 1% Calcium dinonylnaphthalene sulfonate + 1% (BuO)₃P + 1% H₂SO₄ in base oil | 0.99 |

TABLE 4

Four-Ball Wear Test

| Item | Wear Scar Diameter in mm, 30 Minute Test, 60 kg Load, 2000 RPM, 200 F. |
|---|---|
| Base oil (80% solvent paraffinic bright, 20% solvent paraffinic neutral mineral oils) | 4.10 |
| 1% of example 1 | 2.42 |
| 1% of example 2 | 2.26 |
| 1% of example 3 | 2.28 |

The results of Table 3 clearly illustrate the improvement in antiwear properties of item 1 sulfonate/phosphite mixture when acidified during test operation as shown in items 2 and 3 exhibiting much less wear than non-acidified mixture. The wear scar diameter decreased from 2.00 mm to as low as 0.57 mm via the in-situ neutralization technique.

Table 4 illustrates the antiwear properties of the products of Examples 1, 2, and 3 pre-acidified in the laboratory prior to measurement of antiwear properties.

We claim:

1. A process for making a reaction product suitable for use as an additive in lubricating oils comprising reacting a metal dihydrocarbylaromatic sulfonate and a dihydrocarbyl or trihydrocarbyl phosphite in a mole ratio of sulfonate compound to phosphite compound of between about 10:1 and about 1:10 at a temperature between about 30° C. and about 250°.

2. The process of claim 1 wherein the metal dihydrocarbylaromatic sulfonate compound is a compound of a metal selected from the group consisting of calcium, barium, sodium, magnesium, and lithium.

3. The process of claim 1 wherein the metal dihydrocarbylaromatic sulfonate compound is a dialkylnaphthalene sulfonate compound of a metal selected from the group consisting of calcium, barium, sodium, magnesium, and lithium.

4. The process of claim 3 wherein the dialkylnaphthalene sulfonate compound is a compound of calcium.

5. The process of claim 3 wherein the metal dihydrocarbylaromatic sulfonate compound is calcium dinonylnaphthalene sulfonate.

6. The process of claim 3 wherein the dialkylnaphthalene sulfonate has a sulfonate group attached to one ring of a naphthalene nucleus and an alkyl group attached to each ring, each alkyl group independently containing from about six to about twenty carbon atoms, the dialkylnaphthalene sulfonate group being attached to the metal through the sulfonate group and in the case of monovalent metals, one dialkylnaphthalene sulfonate group being attached to each metal atom and there being two groups attached to each atom of a divalent metal.

7. The process of claim 3 wherein the dihydrocarbyl or trihydrocarbyl phosphite has the structural formula $$(R_1O)_2POR_2$$

where $R_1$ is a hydrocarbon radical of 2 to 18 carbon atoms and $R_2$ is hydrogen or a hydrocarbon radical of 2 to 18 carbon atoms.

8. The process of claim 3 wherein the dihydrocarbyl or trihydrocarbyl phosphite is selected from the group consisting of oleyl, phenyl, nonyl phenyl, octylphenyl, 1-ethyl hexyl, 1,3-dimethylbutyl, tridecyl, isodecyl, octyl, and butyl, and mixed phosphite thereof.

9. The reaction product produced by the process of claim 1.

10. The reaction product produced by the process of claim 2.

11. The reaction product produced by the process of claim 3.

12. The reaction product produced by the process of claim 4.

13. The reaction product produced by the process of claim 5.

14. The reaction product produced by the process of claim 6.

15. The reaction product produced by the process of claim 7.

16. The reaction product produced by the process of claim 8.

17. A lubricant composition comprising a lubricant and between about 0.01% and about 10% by weight of the total composition of the reaction product resulting from the process of claim 1.

18. A lubricant composition comprising a lubricant and between about 0.01% and about 10% by weight of the total composition of the reaction product resulting from the process of claim 2.

19. A lubricant composition comprising a lubricant and between about 0.01% and about 10% by weight of the total composition of the reaction product resulting from the process of claim 3.

20. A lubricant composition comprising a lubricant and between about 0.01% and about 10% by weight of the total composition of the reaction product resulting from the process of claim 4.

21. A lubricant composition comprising a lubricant and between about 0.01% and about 10% by weight of the total composition of the reaction product resulting from the process of claim 5.

22. A lubricant composition comprising a lubricant and between about 0.01% and about 10% by weight of the total composition of the reaction product resulting from the process of claim 6.

23. A lubricant composition comprising a lubricant and between about 0.01% and about 10% by weight of the total composition of the reaction product resulting from the process of claim 7.

24. A lubricant composition comprising a lubricant and between about 0.01% and about 10% by weight of the total composition of the reaction product resulting from the process of claim 8.

25. A method for making a lubricant composition comprising adding to a lubricant between about 0.01% and about 10% by weight of the total composition of the reaction product resulting from the process of claim 1.

26. An additive composition for lubricating oils comprising an acid or acid-supplying source and a reaction product resulting from reacting a metal dihydrocarbylaromatic sulfonate and a dihydrocarbyl or trihydrocarbyl phosphite in a mole ratio of sulfonate compound to phosphite compound of between about 10:1 and about 1:10 at a temperature between about 60° C. and about 200°.

27. The additive composition of claim 26 wherein the metal dihydrocarbylaromatic sulfonate compound is a compound of a metal selected from the group consisting of calcium, barium, sodium, magnesium, and lithium.

28. The additive composition of claim 26 wherein the metal dihydrocarbylaromatic sulfonate compound is a dialkylnaphthalene sulfonate compound of a metal selected from the group consisting of calcium, barium, sodium, magnesium, and lithium.

29. The additive composition of claim 28 wherein the dialkylnaphthalene sulfonate compound is a compound of calcium.

30. The additive composition of claim 27 wherein the metal dihydrocarbylaromatic sulfonate compound is calcium dinonylnaphthalene sulfonate.

31. The additive composition of claim 27 wherein the dihydrocarbyl or trihydrocarbyl phosphite has the structural formula $(R_1O)_2POR_2$ where $R_1$ is a hydrocarbon radical of 4 to 18 carbon atoms and $R_2$ is hydrogen or a hydrocarbon radical of 4 to 18 carbon atoms.

32. The additive composition of claim 27 wherein the dihydrocarbyl or trihydrocarbyl phosphite is selected from the group consisting of oleyl, phenyl, nonyl phenyl, octylphenyl, 1-ethyl hexyl, 1,3-dimethylbutyl, tridecyl, isodecyl, octyl, and butyl, and mixed phosphites thereof.

33. The additive composition of claim 26 wherein the acid or acid supplying source is selected from the group consisting of inorganic or organic acids.

34. A lubricant composition comprising a lubricant and between about 0.01% and about 10% by weight of the total composition of the reaction product of claim 26.

35. A lubricant composition comprising a lubricant and between about 0.01% and about 10% by weight of the total composition of the reaction product of claim 27.

36. A lubricant composition comprising a lubricant and between about 0.01% and about 10% by weight of the total composition of the reaction product of claim 28.

37. A lubricant composition comprising a lubricant and between about 0.01% and about 10% by weight of the total composition of the reaction product of claim 29.

38. A lubricant composition comprising a lubricant and between about 0.01% and about 10% by weight of the total composition of the reaction product of claim 30.

39. A lubricant composition comprising a lubricant and between about 0.01% and about 10% by weight of the total composition of the reaction product of claim 31.

40. A lubricant composition comprising a lubricant and between about 0.01% and about 10% by weight of the total composition of the reaction product of claim 32.

41. A method for making a lubricant composition comprising adding to a lubricant between about 0.01% and about 10% by weight of the total composition of the additive composition of claim 33.

42. A composition suitable for use as an additive in lubricating oils comprising a mixture of a dihydrocarbylaromatic sulfonic acid and a dihydrocarbyl or trihydrocarbyl phosphite in a mole ratio of sulfonic acid to phosphite compound of between about 10:1 and about 1:10.

43. The composition of claim 42 wherein the sulfonic acid is selected from the group consisting of alkylated naphthylene sulfonic acids and alkylated benzenesulfonic acids.

44. The composition of claim 42 wherein the sulfonic acid is dinonylnaphthalene sulfonic acid.

45. The composition of claim 42 wherein the dihydrocarbyl or trihydrocarbyl phosphite has the structural formula $(R_1O)_2POR_2$ where $R_1$ is a hydrocarbon radical of 4 to 18 carbon atoms and $R_2$ is hydrogen or a hydrocarbon radical of 4 to 18 carbon atoms.

46. The composition of claim 42 wherein the dihydrocarbyl or trihydrocarbyl phosphite is selected from the group consisting of oleyl, phenyl, nonyl phenyl, octylphenyl, 1-ethyl hexyl, 1,3-dimethylbutyl, tridecyl, isodecyl, octyl, and butyl, and mixed phosphites thereof.

47. A lubricant composition comprising a lubricant and between about 0.01% and about 10% by weight of the total composition of the mixture of claim 42.

48. A lubricant composition comprising a lubricant and between about 0.01% and about 10% by weight of the total composition of the mixture of claim 43.

49. A lubricant composition comprising a lubricant and between about 0.01% and about 10% by weight of the total composition of the mixture of claim 44.

50. A method for making a lubricant composition comprising adding to a lubricant between about 0.01% and about 10% by weight of the total composition of the mixture of claim 44.

* * * * *